(12) United States Patent
Pfirrmann

(10) Patent No.: US 8,030,301 B2
(45) Date of Patent: Oct. 4, 2011

(54) TREATMENT OF CANCERS WITH METHYLOL-CONTAINING COMPOUNDS AND AT LEAST ONE ELECTROLYTE

(75) Inventor: Rolf W. Pfirrmann, Lucerne (CH)

(73) Assignee: Ed. Geistlich Soehne AG Fuer Chemische Industrie, Wolhusen (CH)

( * ) Notice: Subject to any disclaimer, the term of this patent is extended or adjusted under 35 U.S.C. 154(b) by 0 days.

(21) Appl. No.: 11/313,846

(22) Filed: Dec. 22, 2005

(65) Prior Publication Data

US 2006/0160792 A1 Jul. 20, 2006
US 2010/0081649 A9 Apr. 1, 2010

Related U.S. Application Data

(60) Continuation-in-part of application No. 10/950,672, filed on Sep. 28, 2004, now abandoned, which is a continuation-in-part of application No. 10/253,907, filed on Sep. 25, 2002, now Pat. No. 6,821,968, said application No. 10/950,672 is a continuation-in-part of application No. 10/934,474, filed on Sep. 7, 2004, which is a division of application No. 10/109,058, filed on Mar. 29, 2002, now abandoned, application No. 11/313,846, which is a continuation-in-part of application No. 10/424,102, filed on Apr. 28, 2003, which is a continuation of application No. 10/281,138, filed on Oct. 28, 2002, now Pat. No. 6,815,441, which is a division of application No. 09/583,902, filed on Jun. 1, 2000, now Pat. No. 6,479,481.

(60) Provisional application No. 60/280,748, filed on Apr. 3, 2001, provisional application No. 60/281,710, filed on Apr. 6, 2001, provisional application No. 60/281,711, filed on Apr. 6, 2001, provisional application No. 60/281,712, filed on Apr. 6, 2001, provisional application No. 60/281,713, filed on Apr. 6, 2001, provisional application No. 60/284,933, filed on Apr. 20, 2001, provisional application No. 60/284,934, filed on Apr. 20, 2001, provisional application No. 60/182,200, filed on Feb. 14, 2000, provisional application No. 60/137,421, filed on Jun. 4, 1999, provisional application No. 60/151,050, filed on Aug. 27, 1999, provisional application No. 60/167,681, filed on Nov. 29, 1999, provisional application No. 60/174,607, filed on Jan. 5, 2000.

(51) Int. Cl.
*A61K 31/54* (2006.01)
(52) U.S. Cl. ............... 514/222.5; 514/885; 514/908
(58) Field of Classification Search ............... 514/222.5, 514/885, 908
See application file for complete search history.

(56) References Cited

U.S. PATENT DOCUMENTS

| | | |
|---|---|---|
| 504,243 A | 8/1893 | Philippot |
| 1,039,140 A | 9/1912 | Kampfe |
| 1,188,697 A | 6/1916 | Steinberg |
| 1,461,366 A | 7/1923 | Mulford et al. |
| 1,676,146 A | 7/1928 | Krafft |
| 2,021,465 A | 11/1935 | Ritscher |
| 2,609,960 A | 9/1952 | Irwin |
| 2,643,024 A | 6/1953 | Cronheim |
| 2,760,672 A | 8/1956 | Cronheim |
| 3,598,105 A | 8/1971 | Cristaldi |
| 3,809,064 A | 5/1974 | Ziegler |
| 3,961,443 A | 6/1976 | Insalaco |
| 4,000,830 A | 1/1977 | French |
| 4,350,156 A | 9/1982 | Malchesky et al. |
| 4,467,784 A | 8/1984 | Lee et al. |
| 4,482,077 A | 11/1984 | Henderson |
| 4,626,536 A | 12/1986 | Pfirrmann |
| 4,654,345 A | 3/1987 | Cavanak |
| 4,828,140 A | 5/1989 | Henderson |
| 4,960,415 A | 10/1990 | Reinmüller |
| 5,077,281 A | 12/1991 | Reinmüller |
| 5,167,960 A | 12/1992 | Ito et al. |
| 5,176,651 A | 1/1993 | Allgood et al. |
| 5,191,900 A | 3/1993 | Mishra |
| 5,208,018 A | 5/1993 | Gough |

(Continued)

FOREIGN PATENT DOCUMENTS

| | | |
|---|---|---|
| CA | 2302720 A1 | 9/2000 |
| CA | 2 393 159 A1 | 6/2001 |
| CA | 2 393 252 A1 | 6/2001 |
| CH | 587040 A5 | 4/1977 |
| DE | 3536560 A1 | 4/1986 |

(Continued)

OTHER PUBLICATIONS

University of Florida Shands Cancer Center (www.ufscc.ufl.edu/Patient/content.aspx (pp. 1-3) (2006).*

(Continued)

*Primary Examiner* — Brandon Fetterolf
*Assistant Examiner* — Shirley V Gembeh
(74) *Attorney, Agent, or Firm* — Rothwell, Figg, Ernst & Manbeck, P.C.

(57) ABSTRACT

A method of inhibiting growth of a tumor cell in a mammal may include steps of administering to the mammal a first solution including a tumor-inhibiting methylol-containing compound, the first solution further including a first combination having a plurality of physiologically acceptable electrolytes or a second combination having at least one amino acid in combination with at least one physiologically acceptable electrolyte. Alternatively, another solution may be administered to the mammal containing a tumor-inhibiting methylol-containing compound, while concurrently administering to the mammal a further solution including the first combination with the plurality of physiologically acceptable electrolytes or the second combination with at least one said amino acid in combination with at least one physiologically acceptable electrolyte.

31 Claims, No Drawings

U.S. PATENT DOCUMENTS

| | | | |
|---|---|---|---|
| 5,210,083 A | 5/1993 | Pfirrmann | |
| 5,262,403 A | 11/1993 | Nicolson et al. | |
| 5,362,754 A | 11/1994 | Raad et al. | |
| 5,416,091 A | 5/1995 | King | |
| 5,441,481 A | 8/1995 | Mishra et al. | |
| 5,554,148 A | 9/1996 | Aebischer et al. | |
| 5,593,665 A | 1/1997 | Pfirrmann et al. | |
| 5,696,153 A | 12/1997 | Ainsworth et al. | |
| 5,725,553 A | 3/1998 | Moenning | |
| 5,730,045 A | 3/1998 | Delaquis et al. | |
| 5,749,859 A | 5/1998 | Powell | |
| 5,763,421 A | 6/1998 | Caretto et al. | |
| 5,819,748 A | 10/1998 | Pfirrmann | |
| 5,881,905 A | 3/1999 | Brady | |
| 5,889,183 A | 3/1999 | Herdeis et al. | |
| 5,957,038 A | 9/1999 | Shimazaki | |
| 6,011,030 A | 1/2000 | Pfirrmann | |
| 6,029,843 A | 2/2000 | Kroscher et al. | |
| 6,030,358 A | 2/2000 | Odland | |
| 6,035,766 A | 3/2000 | Schirmer | |
| 6,080,397 A * | 6/2000 | Pfirrmann | 424/78.08 |
| 6,093,180 A | 7/2000 | Elsberry | |
| 6,105,811 A | 8/2000 | Alfred | |
| 6,117,868 A | 9/2000 | Pfirrmann | |
| 6,166,007 A | 12/2000 | Sodemann | |
| 6,258,797 B1 | 7/2001 | Lehner | |
| 6,303,596 B1 | 10/2001 | Morrissey et al. | |
| 6,429,224 B1 | 8/2002 | Calabresi et al. | |
| 6,479,481 B1 | 11/2002 | Stendel et al. | |
| 6,521,616 B2 | 2/2003 | Calabresi et al. | |
| 6,546,849 B1 | 4/2003 | Shimazaki | |
| 6,617,333 B2 | 9/2003 | Rabindran et al. | |
| 6,688,487 B2 | 2/2004 | Oakes et al. | |
| 6,815,441 B2 * | 11/2004 | Stendel et al. | 514/222.5 |
| 6,821,968 B2 * | 11/2004 | Pfirrmann | 514/222.5 |
| 6,995,164 B2 | 2/2006 | Calabresi et al. | |
| 7,151,099 B2 | 12/2006 | Redmond et al. | |
| 7,345,039 B2 | 3/2008 | Redmond et al. | |
| 2001/0031870 A1 | 10/2001 | Soll et al. | |
| 2002/0052366 A1 | 5/2002 | Calabresi et al. | |
| 2002/0091123 A1 | 7/2002 | Redmond et al. | |
| 2002/0098164 A1 | 7/2002 | Redmond et al. | |
| 2002/0111328 A1 | 8/2002 | Redmond et al. | |
| 2002/0111345 A1 | 8/2002 | Calabresi et al. | |
| 2002/0131935 A1 | 9/2002 | Fisher et al. | |
| 2003/0027818 A1 | 2/2003 | Redmond et al. | |
| 2003/0092707 A1 | 5/2003 | Redmond et al. | |
| 2003/0195198 A1 | 10/2003 | Stendal et al. | |
| 2004/0087579 A1 | 5/2004 | Redmond et al. | |

FOREIGN PATENT DOCUMENTS

| | | |
|---|---|---|
| DE | 19606897 A1 | 8/1997 |
| EP | 0048558 A2 | 3/1982 |
| EP | 0139535 A2 | 5/1985 |
| EP | 0147021 A1 | 7/1985 |
| EP | 0 253 662 A1 | 1/1988 |
| EP | 1040841 A1 | 10/2000 |
| EP | 1 066 830 A2 | 1/2001 |
| EP | 1201247 A2 | 5/2002 |
| EP | 1247524 A1 | 10/2002 |
| GB | 2165752 A | 4/1986 |
| JP | 60-105618 A | 6/1985 |
| JP | 61-000017 A | 1/1986 |
| JP | 63-72626 A | 4/1988 |
| JP | 5-500973 A | 2/1993 |
| JP | 5-505615 A | 8/1993 |
| JP | 2000-300661 A | 10/2000 |
| JP | 2000-516196 A | 12/2000 |
| JP | 2001-10976 A | 1/2001 |
| JP | 2002-326936 A | 11/2002 |
| WO | WO 88/05301 A1 | 7/1988 |
| WO | WO 91/13628 A1 | 9/1991 |
| WO | WO 92/00743 A1 | 1/1992 |
| WO | WO 95/18638 A1 | 7/1995 |
| WO | WO 95/30423 A2 | 11/1995 |
| WO | WO 97/25052 A2 | 7/1997 |
| WO | WO 98/28027 A1 | 7/1998 |
| WO | WO 98/39354 A1 | 9/1998 |
| WO | WO 98/52572 A1 | 11/1998 |
| WO | WO 99/06114 A2 | 2/1999 |
| WO | WO 00/01391 A1 | 1/2000 |
| WO | WO 01/39762 A3 | 6/2001 |
| WO | WO 01/39763 A2 | 6/2001 |
| WO | WO 02/07810 A2 | 1/2002 |

OTHER PUBLICATIONS

Braumann et al (Clinical Exper. Metastasis) 2003;20(5):387-94.*
Wicki et al. ("Taurolin: A New Concept in Antimicrobial Chemotherapy in Surgical Infection" Urban and Scwarzenbern, vol. 111, pp. 244-253).*
http://www.nlm.nih.gov/medlineplus/ency/article/002467.htm Jun. 9, 2001.*
van Gelder Neurochemical Research, 8(5) 1983, 687-699.*
Gavrovskaya et al., Institute of Experimental Medicine, the Russian Academy of Medical Sciences, St.Petersburg 197376, Russia (523-528).*
Braumann et al. (Clinical & Exp. Matastasis, 2003, 20;387-394).*
Lubec et al. Life Sciences 58: 2317-2325 (1996).*
Canadian Office Action, Application No. CA 2 379 734 dated Sep. 29, 2008.
Japanese Office Action entitled "Preliminary Notice of Reasons for Rejection", Dec. 4, 2008, and English language translation, pp. 1-7.
European Search Report from EP appln. No. 01 30 9983 dated Apr. 9, 2003, 4 pages.
Ananthan, in *Cancer Chemotherapeutic Agents*, Foye (Ed.), *American Chem. Soc.*, Washington, D.C. (1995) pp. 49-58.
Anderson et al., "The Role of cytokines, Adhesion Molecules, and Chemokines in Interleukin-2-induced Lymphocytic Infiltration in C57BL/6 Mice" *J. Clin. Inv.* 97: 1952-1959, 1996.
Anonymous, "Cerebrospinal Fluid" http://uscneurosurgery.com/infonet/glossary/c/cerebrospinal%20/fluid%20csf.htm. 2 pages. Accessed May 31, 2007.
Anonymous, "Methods of Sterilisation." *British Pharmacopoeia*. vol. 2, Appendix XVIII: A264-A267, 1998.
Anonymous, "Taurolin Suppresses Activity of Tumor Necrosis Factor-$\alpha$ in vivo" Institute of Pharmacology, University of Zurich, Research Report, 1-9, 1993.
Araki et al., *J. Jap. Soc. Gastroenterol. Surg.* 27(5): 1090-1093, 1994.
Bedrosian, I., et al., "Taurolidine, an Analogue of the Amino Acid Taurine, Suppresses Interleukin 1 and Tumor Necrosis Factor Synthesis in Human Peripheral Blood Mononuclear Cells" Cytokine vol. 3, No. 6 (Nov.) 1991: 568-575.
Blenkharn, "The Antimicrobial Activity of Taurolin® —a Possible New Additive for Parenteral Nutrition Solutions" *Clin. Nutr.* 6(1): 35-38, 1987.
Blum et al., "Hexamethylmelamine—A New Drug with Activity in Solid Tumors" *Eur. J. Cancer*, 9:195-202, 1973.
Bobrich et al., "Influence of intraperitoneal application of taurolidine/heparin on expression of adhesion molecules and colon cancer in rats undergoing laparoscopy" *J. Surg. Res.* 137(1):75-82, 2007.
Braumann et al., "The Influence of Intraoperative Intravenous and Intraperitoneal Application of Taurolidine with Heparin on Subcutaneous and Intraperitoneal Tumor Growth in Laparoscopic Surgery in a Rat Model" Dept. of Surgery, Humboldt-University of Berlin, Campus Chartié Mitte, Schumannstr. 20-21, 10098 Berlin, Germany, Apr. 14$^{th}$ and 15$^{th}$, 2000, 3 pages.
Braumann et al., "Influence of intraperitoneal and systemic application of taurolidine and taurolidine/heparin during laparoscopy on intraperitoneal and subcutaneous tumour growth in rats" *Clin. Exp. Metastasis* 18: 547-552, 2001.
Braumann et al., "The Tumor-Suppressive Reagent Taurolidine is an Inhibitor of Protein Biosynthesis" *Int. J. Cancer*, 112: 225-230, 2004.
Braumann et al., "Effects of increasing doses of a bolus injection and an intravenous long-term therapy of taurolidine on subcutaneous (metastatic) tumor growth in rats" *Clin. Exp. Metastasis*, 22: 77-83, 2005.
Braumann et al., "High Doses of Taurolidine Inhibit Advanced Intraperitoneal Tumor Growth in Rats", *J. Surg. Res.* 129: 129-135, 2005.

Braumann et al., "Prevention of disease progression in a patient with a gastric cancer-re-recurrence. Outcome after intravenous treatment with the novel antineoplastic agent taurolidine. Report of a case" *World J. Surg. Oncol.* 4(34): 6 pages, 2006.

Braumann et al., "The Tumor Suppressive Reagent Taurolidine Inhibits Growth of Malignant Melanoma—a Mouse Model" Journal of Surgical Research, vol. 143, (2007), pp. 372-378.

Calabresi et al., "Taurolidine: Cytotoxic and Mechanistic Evaluation of a Novel Antineoplastic Agent" *Can. Res.* 61: 6816-6821, 2001.

Campbell et al., "The Role of Tumor Rejection Antigens in Host Antitumor Defense Mechanisms" *Cancer*, 75(11): 2649-2655, 1995.

Carter et al., *Chemotherapy of Cancer*, Second Ed., John Wiley & Sons, New York, 71-78, 1981.

Clark, K., et al., "KRN8602 (MX2-hydrochloride): an Active New Agent for the Treatment of Recurrent High-grade Glioma" *J. Clin. Oncol.* 17(8): 2579-84, 1999.

Da Costa et al., "The effect of laparotomy and laparoscopy on the establishment of spontaneous tumor metastases" *Surgery*, 124(3): 516-525, 1998.

Da Costa et al., "Laparotomy and laparoscopy differentially accelerate experimental flank tumour growth" *Br. J. Surg.* 85: 1439-1442, 1998.

Da Costa et al., "Taurolidine Improves Survival by Abrogating the Accelerated Development and Proliferation of Solid Tumors and Development of Organ Metastases from Circulating Tumor Cells Released Following Surgery" *J. Surg. Res.* 101:111-119, 2001.

Darnowski et al., "Mechanistic and antineoplastic evaluation of taurolidine in the DU145 model of human prostate cancer" *Can. Chemother. Pharmacol*, 54: 249-258, 2004.

Dimmock, Jr, et al., "Mannich Bases of Phenolic Azobenzenes Possessing Cytotoxic Activity" Eur. J. Med. Chem. (1997) 32, 583-594.

Edwards et al., "Pentoxifylline Inhibits Interleukin-2-induced Toxicity in C57BL/6 Mice but Preserves Antitumor Efficacy" *J. Clin. Inv.* 90: 637-641, 1992.

Embase *J. Surg. Res.* 59: 6: 764-771, 1995.= Treutner.

Endoh, "Effects of Recombinant Interleukin-2 (rIL-2) for Recurrent and Metastatic Renal Cell Carcinoma" *Biotherapy*, 5(6): 1100-1106, 1991.

Erb et al., "Structural Investigation of a New Organic Antiseptic: Taurolidine" *Talanta*, 29: 953-958, 1982.

Erb et al., "Structural investigation of a new organic antiseptic: Taurolidine Analytical study and application to identification and quantitation in biological fluids" *Eur. J. Drug Metab. Pharm.* 8(2): 163-173, 1983.

Fanning et al., "Inhibition of neutrophils apoptosis after elective surgery" *Surgery*, pp. 527-534, 1999.

Fiedler, in *Lexikon der Hilfsstoffe für Pharmazie, Kosmetik und angrenzende Gebiete*, Editio Cantor Aulendorf, 695, 1985.

Finnegan et al., "Taurine Attenuates Recombinant Interleukin-2-Activated, Lymphocyte-Mediated Endothelial Cell Injury" *Cancer*, 82(1): 186-199, 1998.

Fukushima, "Merck Manual, 17th Edition in Japanese" Nikkei BP, pp. 983-992, 1999 (partial English translation).

Gallagher et al., "Hepatic Resection of Solitary Metastasis from Transitional Cell Carcinoma of the Bladder" *J. Urology*, 159: 986, 1998.

Glesby et al., "Pilot Study of Low Dose Daily Interleukin-2 Plus Pegylated-Interferon-alfa-2b and Ribavirin in Patients with HCV/HIV Co-infection: ACTG A5088" 11th Conf. Retrovir Opportunistic Infect., Abstract 818, 1-2, 2004.

Gugenheim et al., "Laparoscopic Resection of Solid Liver Tumours" *Br. J. Surg.*, 83: 334-335, 1996.

Hansen et al., "Altretamine" *The Annals of Pharmacotherapy*, 25:146-152, 1991.

Hood et al., "Studies of the thiadiazine, Taurolidine-I. Identification of the Molecular Species Present in Aqueous Solutions by $^1$H- and $^{13}$C-NMR Spectroscopy", *Talanta*, 41(1): 107-113,1994.

Huscher et al., "Laparoscopic Colorectal Resection", *Surg. Endosc.* 10: 875-879, 1996.

Jacobi et al., "Inhibition of Peritoneal Tumor Cell Growth and Implantation in Laparoscopic Surgery in a Rat Model", Am J of Surgery, 174: 359-363, 1997.

Jacobi et al., "Peritoneal Instillation of Taurolidine and Heparin for the Prevention of Intraperitoneal Tumor Growth and Trocar Metastates in Laparoscopic Operations Using Rats as a Model", *Langenbecks Arch.Chir.*, 382 (Suppl 1): 31-36, 1997.

Jacobi et al., "Influence of different gases and intraperitonial instillation of antiadherent or cytotoxic agents on peritoneal tumor cell growth and implantation with laparoscopic surgery in a rat model", *Sug. Endosc.*, 13: 1021-1025, 1999.

Jacobi et al., "New Therapeutic Strategies to Avoid Intra- and Extraperitoneal Metastases during Laparoscopy: Results of a Tumor Model in a Rat", *Dig. Surg.*, 16: 393-399, 1999.

Jacobi et al., "Taurolidine- a new drug with anti-tumor and anti-angiogenic effects", *Anti-Cancer Drugs*, 16(9): 917-921, 2005.

Jacobs et al. "Interleukin-2 or Autologous Lymphokine-activated Killer Cell Treatment of Malignant Glioma: Phase I Trial" *Cancer Res.* 46 (4 pt 2): 2101-2104, 1986.

Janik et al., "Prevention of Postoperative Peritoneal Adhesions, Efficacy of Povidone", *Arch Surg.*, 117: 1321-1324, 1982.

*The Japanese Journal of Gastroenterological Surgery*, 23(2): 3 pages, 1990.

*The Japanese Journal of Gastroenterological Surgery*, 24(2): 2 pages, 1991.

*The Japanese Journal of Gastroenterological Surgery*, 30(6): 3 pages, 1997.

Johnston et al., "Taurolin for the Prevention of Parenternal Nutrition Related Infection: Antimicrobial Activity and Long-Term Use", *Clin. Nutr.* 12(6): 365-368, 1993.

Kilian et al., "Effects of taurolidine and octreotide on tumor growth and lipid peroxidation after staging-laparoscopy in ductal pancreatic cancer", *Prostaglandins, Leukotrienes and Essential Fatty Acids*, 69: 261-267, 2003.

Kilian et al., "Impact of taurolidin and octreotide on liver metastasis and lipid peroxidation after laparoscopy in chemical induced ductal pancreatic cancer", *Investigational New Drugs*, 23: 157-164, 2005.

Kimura et al., "A Phase III Randomized Study of Interleukin-2 Lymphokine-Activated Killer Cell Immunotherapy Combined with Chemotherapy or Radiotherapy after Curative or Noncurative Resection of Primary Lung Carcinoma" *Cancer*, 80: 42-49, 1997.

Kirsch et al., "The Effect of Polyvinylpyrrolidine on the Stability of Taurolidine", *Pharm. Devel. and Tech.*, 2(4): 345-356. 1997.

Koike et al., "Effect of 48-hour Continuous Intravenous Injection of 5-Flouorouracil (5-FU) for Hematogenous Metastasis of Large Intestine Carcinoma", *Jap. J. Gastro. Surg.* 24(2): 1-3, 1991 (partial English translation).

Koldehoff et al., "Taurolidine is effective in the treatment of central venous catheter-related bloodstream infections in cancer patients", *Intl. J. Antimicrobial Agents*, 24: 491-495, 2004.

Kopple et al., "Effect of Intravenous Taurine Supplementation on Plasma, Blood Cell, and Urine Taurine Concentrations in Adults Undergoing Long-term Parenteral Nutrition[1-3]", *Am. J. Clin. Nutr.*, 52(5): 846-853, 1990.

Lubec et al., "Decreased Tumor Incidence and Increased Survival by One Year Oral Low Dose Arginine Supplementation in the Mouse" Life Sci. 58:2317-2325, 1996.

Lucarotti et al., "Antiseptic Toxicity to breast carcinoma in tissue culture an adjuvant to conservation therapy", *Ann. Roy. Coll. of Surg. of Eng.*, 72: 388-392, 1990.

Lung Cancer, The 38th Japan Lung Cancer Conference, The Japan Lung Cancer Society, 37(5):765, 1997.

McNamara et al., "Significance of angiogenesis in cancer therapy", *Br. J. Surg.* 85: 1044-1055, 1998.

Medical Encyclopedia: Electrolytes http://www.nlm.nih.gov/medlineplus/ency/article/002350.htm, 1, 2001. Accessed May 31, 2007.

Med. J. Kinki Univ., Kinki University Medical Conference, 25(1): 17A, 2000.

Monson, "Malignant Melanoma: A Plague of our Times", *Br. J. Surg.*, 76: 997-998, 1989.

Monson, J.R.T., et al., "Abrogation of tumor necrosis factor (TNF) toxicity in the murine model by taurolidine: support for synergism of TNF with endotoxin", *Br. J. Surg.* 77(6): A708, 1990.

Monson, J.R.T., et al., "Preliminary Evidence that Taurolidine is anti-neoplastic as well as anti-endotoxin and anti-microbial" *Br. J. Surg.* 77(6): A711, 1990.

Monson, J.R.T., et al., "Taurolidine As An Anti-neoplastic Agent: A Previously Undiscovered role?" *Br. J. Surg.* 77(12): 1432, 1990.

Monson, J.R.T., et al., "Taurolidine inhibits tumour necrosis factor (TNF) toxicity—new evidence in TNF and endotoxin synergy?" *Euro. J. Surg. Oncol.* 19: 226-231, 1993.

Morgan-McCourt et al., "Taurolodine inhibits tumor cell growth in vitro and in vivo" *Annals of Surg. Oncol.*, 7(9): 685-691, 2000.

Mughal et al., "Infected Feeding Lines", *Care Critically Ill* 6(6): 228-231, 1990.

Negrier et al., "Interleukin-2 with or without LAK Cells in Metastatic Renal Cell Carcinoma: A Report of a European Multicenter Study" *Eur. J. Cancer Clin. Oncol.* 25: suppl. 3 S21-S28, 1989.

Nestler et al., "Impact of taurolidine on the growth of CC531 colon carcinoma cells in vitro and in a laparoscopic animal model in rats", *Surg. Endosc.*, 19: 280-284, 2005.

Nici et al., "The Effects of Taurolidine, a Novel Antineoplastic Agent, on Human Malignant Mesothelioma", *Clin. Can. Res.* 10: 7655-7661, 2004.

Nudelman et al., "Prodrugs of butyric acid. Novel derivatives possessing increased aqueous solubility and potential for treating cancer and blood diseases", *Eur. J. Med. Chem.* 36: 63-74, 2001.

O'Brien et al., "Co-immunotherapy with interleukin-2 and taurolidine for progressive metastatic melanoma", *Irish J. Med. Sci.* 175(1): 10-15, 2006.

Okuno et al., "Intrahepatic interleukin-2 with chemotherapy for unresectable liver metastases: a randomized multicenter trial" *Hepato-Gastroenterology*, 46(26): 1116-21, Abstract, 1 pg., 1999.

Opitz et al., "The influence of adhesion prophylactic substances and taurolidine/heparin on local recurrence and intraperitoneal tumor growth after laparoscopic-assisted bowel resection of colon carcinoma in a rat model" Surg. Endosc. 17:1098-1104, 2003.

Opitz et al., "Instillation of Taurolidine/Heparin after Laparotomy Reduces Intraperitoneal Tumour Growth in a Colon Cancer Rat Model", *Eur. Surg. Res.* 39: 129-135, 2007.

Opitz et al., "Taurolidine and povidone-iodine induce different types of cell death in malignant pleural mesothelioma" *Lung Cancer*, 56: 327-336, 2007.

Opitz et al., "Local recurrence model of malignant pleural mesothelioma for investigation of intrapleural treatment", *Eur. J. Cardio-thoracic Surg.* 31: 772-778, 2007.

Parfitt, "Martindale, the complete drug reference, $32^{nd}$ ed", (formerly Martindale the extra pharmacopoeia, London: Pharmacopoeia), XP-002231711, London: Pharmaceutical press, GB, 534-537, 1999.

Physicians' Desk Reference, "Fluorouracil Product Information", pp. 2034-2036, 1995.

Pidgeon et al., "The role of endotoxin/lipopolysaccharide in surgically induced tumour growth in a murine model of metastatic disease", *Br. J. Can.* 81(8): 1311-1317, 1999.

Redmond et al., Letter to the Editor, *Annals of Surgery*, 227(2): 309, 1998.

Reinmueller, "Die Beeinflussung der physiologischen und pathologischen Gerinnung durch Taurolidin und Implikationen für die Anwendung", *Zentralbl Chir Suppl*, 4: 13-18, 1999.

Reymond et al., "Feasibility of therapeutic pneumoperitoneum in a large animal model using a microvaporisator", *Surg. Endosc.*, 14: 51-55, 2000.

Ribizzi et al., "Taurolidine: preclinical evaluation of a novel, highly selective, agent for bone marrow purging", *Bone Marrow Transplantation*, 29: 313-319, 2002.

Rodak et al., "Induction of reactive oxygen intermediates-dependent programmed cell death in human malignant ex vivo glioma cells and inhibition of the vascular endothelial growth factor production by taurolidine", *J. Neurosurg.*, 102: 1055-1068, 2005.

Salmaggi et al., "Intrathecal immunotherapy in CNS tumors disseminating via CSF: preliminary evaluation using different treatment schedules" *Italian Journal of Neurological Sciences*, 17: 267-276, 1996.

Semple et al., "Potent and Selective Thrombin Inhibitors Featuring Hydrophobic, Basic $P_3$- $P_4$ aminoalkyllactam Moieties", *Bioorganic & Medicinal Chemistry Let.* 8: 3525-3530, 1998.

Shrayer et al., "The effect of Taurolidine on adherent and floating subpopulations of melanoma cells", *Anti-Cancer Drugs*, 14(4): 295-303, 2003.

Simon et al., "Diagnosis and treatment of catheter-related infections in paediatric oncology: and update", *Clin. Microbiol. Infect.*, 12(7): 606-620, 2006.

Smith, "Interleukin 2 Toxicity—Standard Procedures for Recording & Reporting Drug Toxicities", 1-8, 2000.

Smith et al., "New Strategies to Combat HIV: Augmenting Antiviral Immunity, Rationale for Low-Dose Daily IL-2 Therapy", *AIDS Read.* 13(8): 365-369, 382, 2003.

Stapleton et al., "Taurine and human nutrition", *Clin. Nutr.* 16(3):103-8, 1997.

Stapleton et al., "Taurine and Inflammation—A New Approach to an Old Problem?" *J. of Leukocyte Biol.*, 61: 231-232, 1997.

Stendel et al., "The Effect of Taurolidine on Brain Tumor Cells", *Anticancer Research*, 22: 809-814, 2002.

Stendel, R. et al., "Enhancement of fas-ligand-mediated programmed cell death by taurolidine", *Anticancer Research*, 23: 2309-2314, 2003.

Stendel et al., "Taurolidine-Fibrin-Sealant-Matrix Using Spray Application for Local Treatment of Brain Tumors", *Antican. Res.* 24: 631-638, 2004.

Stendel et al., "Treatment of Glioblastoma with Intravenous Taurolidine. First Clinical Experience", *Antican. Res.* 24: 1143-1148, 2004.

Stendel et al., "Pharmacokinetics of Taurolidine following Repeated Intravenous Infusions Measured by HPLC-ESI-MS?MS of the Derivatives Taurultame and Taurinamide in Glioblastoma Patients", *Clin. Pharmacokinet*, 46(6): 513-524, 2007.

Sun et al., "Taurolidine Induces Apoptosis of Murine Melanoma Cells in Vitro and in Vivo by Modulation of the Bcl-2 Family Proteins", *J. Sur. Oncol.* 96: 241-248, 2007.

Suzuki et al., "An Effective Case of Combined Arterial and Portal Infusion Chemotherapy for SIGMOID Colon Cancer with Multiple Liver Metastases", *Jap. Soc. Gastroent. Surg.* 27(5): 1090-1093, 1994.

Thatcher et al., "Recombinant interleukin-2 (rIL-2) given intrasplenically and intravenously for advanced malignant melanoma. A phase I and II study", *Br. J. Cancer*, 60: 770-774, 1989.

Treutner et al., "Prevention of Postoperative Adhesions by Single Intraperitoneal Medication", *J. Surg. Res.*, 59(6): 764-771, 1995.

Volz,et al., "Modulation of Tumor-Induced Lethality after Pneumoperitoneum in a Mouse Model", *Cancer*, 89(2): 262-266, 2000.

Wakabayashi et al., "Chemotherapy for Brain Tumors", 50(2): 305-312, 2001.

Wang et al., "Endotoxin/Lipopolysaccharide Activates NF-KB and Enhances Tumor Cell Adhesion and Invasion Through a β1 Integrin-Dependent Mechanism", *J. Immunol.*, vol. 170, pp. 795-804, 2003.

Watson et al., "Taurolidine, an antilipopolysaccharide agent, has immunoregulatory properties that are mediated by the amino acid taurine", *J. Leukocyte Biol.* 58: 299-306, 1995.

Weberschock et al., "Efficacy of Sytemic [sic] Taurolidin Application in the Treatment of Liver Metastases in a Rat Model", Dept. of General and Vascular Surgery, Johann Wolfgang Goethe University, 1 page, 1996-2002 (Abstract).

Wenger et al., "Effects of taurolidine and octreotide on port site and liver metastasis after laparoscopy in an animal model of pancreatic cancer", *Clin. & Exp. Metastasis*, 19: 169-173, 2002.

Wittich et al., "Irrigation of Port Sites: Prevention of Port Site Metastases?" *J. Laparoendoscopic & Advanced Surg. Tech.* 14(3): 125-129, 2004.

Wördemann et al., "Tumor Necrosis Factor-α Production by Human Hepatoma Cell Lines Is Resistant to Drugs That Are Inhibitory to Macrophages", *J. Interf. and Cytokine Res.* 18: 1069-1075, 1998.

Wu et al., "Neutrophil-induced Transmigration of Tumour Cells Treated with Tumour-conditioned Medium is Facilitated by Granulocyte-macrophage Colony-stimulating Factor", *Eur. J. Surg.*, 166: 361-366, 2000.

* cited by examiner

TREATMENT OF CANCERS WITH METHYLOL-CONTAINING COMPOUNDS AND AT LEAST ONE ELECTROLYTE

CROSS-REFERENCE TO RELATED APPLICATIONS

This application is a continuation-in-part of U.S. Ser. No. 10/950,672, filed Sep. 28, 2004, which is a continuation-in-part of U.S. Ser. No. 10/253,907, filed Sep. 25, 2002, now U.S. Pat. No. 6,821,968, which claims the benefit of U.S. Provisional Application No. 60/324,533, filed Sep. 26, 2001. U.S. Ser. No. 10/950,672 also is a continuation-in-part of U.S. Ser. No. 10/934,474, filed Sep. 7, 2004, which is a continuation-in-part of U.S. Ser. No. 10/109,058, filed Mar. 29, 2002, which claims the benefit of U.S. Provisional Application No. 60/280,748, filed Apr. 3, 2001, U.S. Provisional Application No. 60/281,710, filed Apr. 6, 2001, U.S. Provisional Application No. 60/281,711, filed Apr. 6, 2001, U.S. Provisional Application No. 60/281,712, filed Apr. 6, 2001, U.S. Provisional Application No. 60/281,713, filed Apr. 6, 2001, U.S. Provisional Application No. 60/284,933, filed Apr. 20, 2001, and U.S. Provisional Application No. 60/284,934, filed Apr. 20, 2001. This application further is a continuation-in-part of U.S. Ser. No. 10/424,102, filed Apr. 28, 2003, which is a continuation of U.S. Ser. No. 10/281,138, filed Oct. 28, 2002, now U.S. Pat. No. 6,815,441 B1, which is a divisional of U.S. application Ser. No. 09/583,902, filed Jun. 1, 2000, now U.S. Pat. No. 6,479,481 B1, which claims benefit of U.S. Provisional Application No. 60/182,200, filed on Feb. 14, 2000, and claims benefit of U.S. Provisional Application No. 60/137,421 filed Jun. 4, 1999, and claims benefit of U.S. Provisional Application No. 60/151,050 filed Aug. 27, 1999, and claims benefit of U.S. Provisional Application No. 60/167,681 filed Nov. 29, 1999, and claims benefit of U.S. Provisional Application No. 60/174,607, filed Jan. 5, 2000.

TECHNICAL FIELD

The invention relates to the use of methylol-containing compounds, such as taurolidine and taurultam, for the treatment of cancer.

BACKGROUND OF THE INVENTION

Methylol transfer agents, such as the antibacterial and antitoxin drug taurolidine and the related product taurultam, have been shown to exert a modifying effect on the toxicity of tumor necrosis factor (TNF) which is used, inter alia, in the treatment of tumors. Furthermore, the action of methylol transfer agents has been shown to be selective in that the growth of normal cell-lines was not significantly inhibited.

Taurolidine acts by transferring three methylol groups at the site of action, taurultam being an intermediate metabolite which itself transfers a single methylol group with liberation of the very well tolerated compound taurinamide. Thus, the two compounds act by essentially the same mechanism. It should be noted that methylol transfer is to be contrasted with methyl transfer which is characteristic of many highly toxic anti-tumor drugs. Taurolidine and taurultam have low toxicity and are not cytotoxic against normal cells.

Programmed cell death is an evolutionary conserved biological principle in the regulation of cell numbers. Sensitive cells contain death receptors which are activated when the appropriate ligands are secreted from neighboring cells. A prominent system in programmed cell death is Fas-ligand mediated apoptosis. Fas, also known as CD 95/APO-l, is a cell surface receptor and a member of the tumor necrosis factor receptor superfamily which mediates apoptosis in sensitive cells upon oligomerization by the Fas-ligand (FasL).

SUMMARY OF THE INVENTION

In accordance with the present invention, a method of inhibiting growth of a tumor cell in a mammal comprises:

A) Administering to said mammal a first solution comprising a tumor-inhibiting methylol-containing compound, said first solution further comprising a first combination comprising a plurality of physiologically acceptable electrolytes or a second combination comprising at least one amino acid in combination with at least one physiologically acceptable electrolyte; or B) administering to said mammal another solution containing said tumor-inhibiting methylol-containing compound, and concurrently administering to said mammal a further solution comprising said first combination comprising said plurality of physiologically acceptable electrolytes or said second combination comprising at least one said amino acid in combination with at least one said physiologically acceptable electrolyte.

DETAILED DESCRIPTION

The present invention relates to the ability of methylol transfer agents, such as taurolidine, to induce cell toxicity, and to enhance Fas-ligand mediated apoptosis in combination therapy. Both taurolidine and its congener taurultam enhance the apoptotic effect of Fas-ligand in cancer cells at drug concentrations which per se show practically no effect on cell viability. In the human malignant glioma cell line LN-229 cell viability was reduced directly following incubation with taurolidine or taurultam alone. This effect enhanced the destruction of LN-229 cells by Fas-ligand. Thus, the use of methylol transfer agents to induce apoptotic cell death provides a means for treating cancer.

The two cell lines LN-18 and LN-229 represent validated model systems for apoptotic cell death with different sensitivities to Fas-ligand. These cell lines were therefore used to test the potential interaction of such compounds with the apoptotic pathway. The viability of the human malignant glioma cells LN-18 and LN-229 is differently affected by taurultam and taurolidine. The LN-18 cells, which are highly sensitive to Fas-ligand induced apoptosis, remained unaffected by taurultam at all concentrations tested (5, 20, 100 µg/ml) (Example 6). Taurolidine was able to only slightly reduce the viability of LN-18 cells at the highest concentration tested (100 µg/ml). Thus, the threshold for the destruction of LN-18 cells was reached at 0.01% of taurolidine. In contrast, LN-229 cells showed a much higher sensitivity to these drugs. In contrast to LN-18 cells, both taurultam and taurolidine by themselves (100 µg/ml) strongly decreased the viability of LN-229 cells. Taurolidine (100 µg/ml) caused a dramatic death of LN-229 cells (70%) and taurultam (100 µg/ml) was able to reduce the viability of LN-229 cells by 30%. At the highest concentration tested (100 µg/ml), taurolidine alone was about as effective as the Fas-ligand in inducing cell death. Thus, taurolidine and taurultam have the ability to destroy human malignant cells.

In accordance with the present invention, a method of treating cancer is provided, whereby apoptotic death of a neoplastic cell may be induced by contacting said cell with an apoptosis-inducing amount of a methylol-containing compound.

One embodiment comprises administration of a methylol transfer agent in at least two dosing cycles, each cycle comprising an administration phase and a non-administration (rest) phase, the administration phase comprising administration, preferably by infusion, of a daily dose of the methylol transfer agent for about 1 to 8 days, followed by a non-administration (rest) phase of about 1 to 14 days during which no methylol transfer agent is administered.

In another embodiment, liver cancer is treated by intravenous infusion of solutions containing a methylol transfer agent, by direct administration through a catheter installed into a hepatic vessel, such as the hepatic artery, the portal vein, or the gastroduodenal artery.

In another embodiment, tumors of the central nervous system, such as glioma/glioblastoma, are treated.

Preferred methylol transfer agents are taurolidine, taurultam, and mixtures thereof.

The method may be carried out by administering to a mammal suffering from cancer, compositions containing an active methylol-containing compound, at a dose sufficient to induce death of neoplastic cells by apoptosis. By "methylol-containing compound," or "methylol transfer agent," is meant a compound which contains or is capable of producing a methylol molecule under physiological conditions. A methylol-containing compound is characterized as having a R—$CH_2$—OH group in which R is an alkyl, aryl or hetero group. The invention also includes the use of compounds capable of producing or being converted into a compound containing a R—$CH_2$—OH structure.

Methylol transfer agents include methylol-containing compounds such as taurolidine and taurultam, and their derivatives. The compounds taurolidine and taurultam are disclosed in U.S. Pat. No. 5,210,083. Other suitable methylol-containing compounds include taurinamide derivatives and urea derivatives. Examples of derivatives of taurolidine, taurultam, taurinamide and urea useful in the present invention can be found in WO 01/39763A2. Particularly preferred methylol transfer agents for utilization in accordance with the present invention are taurolidine, taurultam, biologically active derivatives thereof and mixtures thereof.

Alternatively, the compound is a taurinamide derivative, or a urea derivative. Examples of derivatives of taurolidine, taurultam, taurinamide and urea useful in the present invention can be found in WO 01/39763A2.

Other methylol-containing compounds suitable for inducing apoptotic death of cancer cells include but are not limited to 1,3,-dimethylol-5,5-dimethylhydantoin, hexamethylene tetramine, or noxythiolin. By derivative of taurolidine or taurultam is meant a sulfonamide compound which possesses at least 10% of the neoplastic activity of taurolidine or taurultam, respectively. A sulfonamide compound is one having a $R_2N$—$SO_2R'$ formula. Derivatives of the compounds described herein may differ structurally from a reference compound, e.g., taurolidine or taurultam, but preferably retain at least 50% of the biological activity, e.g., induction of apoptotic cell death, of the reference compound. Preferably, a derivative has at least 75%, 85%, 95%, 99% or 100% of the biological activity of the reference compound. In some cases, the biological activity of the derivative may exceed the level of activity of the reference compound. Derivatives may also possess characteristics or activities not possessed by the reference compound. For example, a derivative may have reduced toxicity, prolonged clinical half-life, or improved ability to cross the blood-brain barrier.

Treatment of an autologous tumor, e.g., a tumor of the central nervous system (CNS), is carried out by administering to a mammal, e.g., a human patient, a methylol-containing compound. The compound is administered systemically, e.g., orally or intravenously, or infused directly to the site of the tumor, e.g., to the brain or cerebrospinal fluid. An erodible or resorbable solid matrix such as a wafer or sponge can be implanted directly into brain tissue.

Cancers to which the present invention may be applicable include glioma, neuroblastoma, astrocytoma, carcinomatous meningitis, ovarian cancer, prostate cancer, central nervous system (CNS) cancer, lung cancer, gastric cancer, esophageal cancer, urinary bladder cancer, leukemia, lymphoma, melanoma, renal cell cancer and metastases thereof. Other cancers against which the method of the present invention is effective include other carcinomas, sarcomas or lymphomas, cancers of the head and neck, liver cancer, breast cancer, mesothelioma and pancreatic cancer.

Particularly preferred embodiments involve treatment of cancers selected from the group consisting of glioma, neuroblastoma, astrocytoma, central nervous system (CNS) cancer, and liver cancer, as well as inhibition of tumor metastases thereof.

It is particularly beneficial to use taurolidine and/or taurultam, at concentrations sufficient to induce apoptosis in cancer cells, to prevent the spread of metastases, especially following surgical removal of tumors. The mammalian subjects are typically humans.

The invention also includes the use of taurolidine and/or taurultam, at concentrations sufficient to induce apoptosis in cancer cells, for the treatment or prophylaxis of tumors in mammalian subjects.

The invention further includes the use of taurolidine and/or taurultam, at concentrations sufficient to induce apoptosis in cancer cells, for the preparation of pharmaceutical compositions for the treatment or prophylaxis of tumors in mammalian subjects by induction of apoptosis.

Effective dosage amounts of a methylol transfer agent in accordance with the present invention may comprise pharmaceutical dosage units within the range of about 0.1-1,000 mg/kg, preferably 150-450 mg/kg per day, and most preferably 300-450 mg/kg per day. Alternatively, the dosages can be administered on a grams/day basis, from about 2-60 g/day. Preferred doses may be in the range of about 2.5-30 g/day taurolidine, 4-60 g/day taurultam, or a mixture thereof. Most preferred doses are in the range of about 10-20 g/day taurolidine, 20-40 g/day taurultam, or a mixture thereof.

Suitable formulations for injection or infusion may comprise an isotonic solution containing one or more solubilizing agents, e.g., polyols such as glucose, in order to provide solutions of increased taurolidine or taurultam concentration. Such solutions are described in EP 253662B1. The concentration of taurolidine or taurultam in such solutions may be in the range 1-60 g/liter.

Methylol transfer agents are generally poorly soluble in water. Thus, it is often required to administer relatively large volumes of aqueous solutions containing taurolidine or taurultam, for example 10 g to 30 g of taurolidine and/or taurultam. Preferred solutions for administration in accordance with the present invention contain from about 0.5-2% taurolidine and/or taurultam. It may be convenient to administer these compounds by infusion in view of the relatively large volumes concerned, conveniently at intervals throughout the day.

In accordance with one embodiment, tumor cell growth in a mammal is inhibited by administering to the mammal a first solution comprising a tumor-inhibiting methylol-containing compound, the first solution further comprising a first combination including a plurality of physiologically acceptable electrolytes or a second combination comprising at least one amino acid in combination with at least one physiologically acceptable electrolyte.

In accordance with a second embodiment, tumor cell growth in a mammal is inhibited by administering to the mammal another solution containing the tumor-inhibiting methylol-containing compound, and concurrently administering to the mammal a further solution comprising the first combination including the plurality of physiologically acceptable electrolytes, or the second combination comprising at least one amino acid in combination with at least one physiologically acceptable electrolyte.

The methylol-containing compound preferably is taurolidine, taurultam or a mixture thereof. When the first above-mentioned solution is administered, the first solution preferably contains the first combination or the second combination at a concentration sufficient to render the first solution substantially isotonic. When the above-mentioned another solution is administered, prior to administration to the mammal, the above-mentioned another solution preferably is blended with the further solution so as to form a mixed solution which is substantially isotonic. A "Y" connector can be utilized for such blending so as to connect a separate bottle of a solution containing the methylol-containing compound with a separate bottle containing the solution of electrolytes or at least one amino acid and at least one electrolyte, to thereby combine the different solutions into a single IV line for delivery to a patient.

The present invention may utilize stable aqueous solutions containing taurolidine at a concentration within the range of about 1.5-3% by weight. The solutions are rendered stable by including therein a stability-enhancing effective amount of at least one physiologically acceptable electrolyte so that the resulting solution is substantially isotonic. Suitable electrolyte(s) provide ions selected from the group consisting of $Na^+$, $K^+$, $Mg^{++}$, $Cl^-$, $H_2PO_4^-$, Acetate$^-$, $HCO_3^-$, and mixtures thereof. In preferred embodiments, the electrolyte(s) are selected from the group consisting of NaCl, KCl, $CaCl_2$, $NaHCO_3$, and mixtures thereof.

In preferred embodiments, taurolidine is present in the solution within a range of about 1.5-2.5% by weight, more preferably within the range of about 1.7-2.3% by weight, even more preferably within the range of about 1.8-2.2% by weight, still more preferably within the range of about 1.9-2.1% by weight, most preferably about 2% by weight.

For example, one composition for use in accordance with the present invention comprises an isotonic ringer solution including about 2% by weight taurolidine. An alternative to use of ringer solution is full electrolyte solution, which contains phosphates not present in ringer solution.

In particularly preferred embodiments, a composition for use in accordance with the present invention additionally includes sufficient physiologically acceptable colloidal material (colloid) so as to also effectively render the inventive solution iso-oncotic. The colloidal material can be polyvinylpyrrolidone (PVP), hydroxy ethyl starch (HES), or the like. Preferred colloidal materials include low molecular weight PVP, having an average molecular weight within the range of about 1,000-15,000, preferably within the range of about 1,000-13,000, more preferably about 9,000. A particularly preferred PVP for use in accordance with the present invention is Kollidon or Povidone. Preferred amounts of colloidal material in the solution are within the range of about 1-10% by weight, preferably about 3-7% by weight, most preferably about 5% by weight.

One preferred solution for use in accordance with the present invention includes the following in percentages by weight in water for injection:
2% taurolidine
5% Kollidon
0.4% NaCl
0.005% KCl
0.0066% $CaCl_2$
0.005% $NaHCO_3$ Isotonic taurolidine solutions for use in accordance with the present invention also can be prepared so as to include at least one amino acid, wherein the amounts of other electrolytes added to the solution are reduced in proportion to the amount of the one or more amino acid(s) added, so as to maintain isotonicity. Preferred amounts of amino acid(s) in the solution are within the range of about 0.1-3% by weight, more preferably within the range of about 0.2-2% by weight, still more preferably within the range of about 0.3-1% by weight, even more preferably within the range of about 0.4-0.6% by weight, most preferably about 0.5% by weight. Taurine is particularly preferred. One exemplary composition in accordance with this embodiment, in water for injection, is as follows in percentages by weight:
2% taurolidine
5% Kollidon
0.5% taurine
0.26% NaCl
0.0033% KCl
0.004% $CaCl_2$
0.003% $NaHCO_3$ Solutions for use in accordance with the invention may have a pH within the range of about 7.1-7.9. The above solution before sterilization has a pH of about 7.8, and after sterilization has a pH of about 7.2-7.38. Ideally, a solution in accordance with the present invention has a pH of about 7.4.

In yet another embodiment, taurultam is substituted for amino acid(s) such as taurine in isotonic taurolidine solutions according to the invention. For example, about 0.1-1% by weight taurultam may be substituted for amino acid(s) such as taurine in isotonic 1.5-3% taurolidine solutions, preferably about 0.2-0.5% by weight taurultam.

Administration, preferably by infusion, of the total daily dose can be carried out at a consistent rate over 24 hours, or according to a more rapid infusion schedule of the dose in portions, with breaks between each portion of the dose, e.g. infusion of 250 ml of a 2% taurolidine solution (5 g dose) over 2 hours, followed by a brief break of 4 hours, repeated over the course of a 24 hour infusion period to achieve a total daily dose of 20 g. Alternatively, 250 ml of a 2% taurolidine solution may be infused over one hour, with a one hour break between dose portions, and repeated until the daily dose is achieved, such that the total daily dose is provided over the course of less than 24 hours (i.e., approximately half the day), with no infusion occurring during the remainder of the day.

In accordance with one embodiment, four bottles (250 ml each) of 2% taurolidine solution are administered intravenously to patients with cancer, at a rate of 40 drops per minute, one bottle every six hours. The therapy cycle generally is an administration phase of daily infusions for one week, followed by a rest phase of two weeks. Total treatment generally is at least two such cycles. Efficacy of taurolidine 2% solution administered intravenously has been found to be particularly good with 25-28 bottles of 250 ml taurolidine 2% solution being instilled per cycle.

In accordance with a second embodiment of the invention, the administration phase comprises a daily regimen whereby 250 ml of taurolidine 2% solution is administered over the course of 2 hours, followed by a four hour break, repeated over 24 hours to achieve the total daily dose.

In accordance with a third embodiment of the invention, the administration phase comprises a daily regimen whereby 250 ml of 2% taurolidine solution is infused over one hour, followed by a one-hour break, and repeated until the daily dose is achieved. If the total dose is 20 g (for example), this regimen would provide the daily dose with four 250 ml infusions of 2% taurolidine over a 7 hour time span. No infusion occurs for the remainder of the day. Infusion rates can be lengthened (e.g., to 250 ml over 90 or 120 minutes) if the patient shows an elevated liver count.

In particularly preferred embodiments, patients are subjected to dosing cycles having an administration phase of at least 1 day, more preferably at least 3 continuous days, and up to about 8 continuous days, each administration phase being followed by a non-administration phase of about 1 day to about 4 weeks, e.g., 1-14 days, or even 3, 4 or more weeks, during which the methylol-containing compound is not administered to the patient. During each administration phase, the methylol-containing compound is administered each day. For example, administration phases of 3, 4, 5, 6, 7 and/or 8 days can be utilized, and non-administration phases of 1, 2, 3, 4, 5, 6, 7, 8, 9, 10, 11, 12, 13, and/or 14 days may be utilized. At least 2 dosing cycles are utilized, preferably 5-10 or more dosing cycles are utilized. For example, 2, 3, 4, 5, 6, 7, 8, 9, 10 or more sequential dosing cycles can be utilized. Such a regimen has shown surprising and unexpected results with patients. In one particularly preferred embodiment, 6 dosing cycles, each with administration phases of 5 days are utilized, with each administration phase separated by a non-administration phase of 2 days. Preferably, during each day of administration, 250 ml of taurolidine 2% solution is intravenously administered to the patient 4 times daily. Such a regimen has surprisingly and unexpectedly resulted in a marked tumor size reduction with disappearance of perifocal edema in a patient with inoperable glioblastoma infiltration of the basal ganglia.

In another embodiment, a non-administration phase may be 1, 2, 3, 4 or more weeks in length, e.g., about 2-4 weeks. For example, in patients with recurrent cancers such as of the stomach and pancreas may be administered sequential dosing cycles having an administration phase of 3-8 continuous days, e.g., 7 days, with, for example, 250 ml taurolidine 2% solution infused 4 times daily, followed by a non-administration phase of 1, 2, 3, 4, or more weeks, e.g., 3 weeks. As in the previous embodiments, at least 2 dosing cycles are utilized, preferably 5-10 or more dosing cycles.

In a further embodiment, concomitant administration of anti-convulsants and/or anti-oedema therapy and/or antibiotics and/or fluid and electrolyte replacement is carried out.

1. Anti-Convulsants

Preferably, the patient should be stabilized on anti-convulsive medications prior to treatment, to avoid complications during the treatment. This can conveniently be administered in part on an out-patient basis, as well as to prevent any emergency stabilization on an undesired medication. Valproinic acid is the agent of first choice; the dose should be determined in accordance with blood level checks and administered in 2 single doses. Normally, a dose of 1200 mg to 1500 mg is required. If a treatment with valproinic acid is not sufficient, a combination treatment with lamotrigin is possible. In case of allergies or if valproinic acid is not tolerated, the primary stabilization is to be done with lamotrigin. Phenyloin and carbamazepin are contra-indicated.

2. Anti-Oedema Therapy

An anti-oedema therapy may also be administered, but only if absolutely necessary, because otherwise focal neurological symptoms may occur or become intensified, or intracerebral pressure may symptoms develop. Dexamethason should be given before or after the taurolidine was administered. The anti-oedema therapy should be administered with dexamethason, using the lowest possible dose. To protect the stomach a concomitant therapy with ranitidine 1×150 mg/day may be given. If stomach problems are observed with this therapy, an alternative treatment with antra 1-2×20 mg/day should be administered.

In cases of massively elevated intracerebral pressure and insufficient effectiveness of dexamethason, a therapy with mannitol, in particular at a dosage of up to 4×250 ml/day, is possible.

3. Antibiotic Therapy

A calculated antibiotic treatment with one of the subsequently listed antibiotics may be given, until the arrival of the sensitivity test.

Urinary Tract Infection:
  primary: Cotrimoxazol
  alternative: Doxycyclin
Pneumonia:
  primary: Erythromycin
  alternative: Doxycyclin The following antibiotics should only be used if absolutely necessary (in the most severe, life-threatening infections) and if the sensitivity situation warrants it: Chino lone, penicillin, cephalosporin 4. Fluid and Electrolyte Replacement in Connection with Intravenous Taurolidine 2% Therapy An amount of 250 ml of full electrolyte solution is preferably be given at the same time and with the same infusion speed parallel to the infusion with 250 ml taurolidine 2%. Electrolytes and blood count should be monitored twice per day, and the central vein pressure should be checked once daily.

If a hypernatraemia is observed, first, it should be determined whether dehydration is the cause. Diuretic agents should only be used if fluid is replaced at the same time and after dehydration was ruled out as the reason.

The methylol-containing compound is administered alone or in combination with one or more additional antineoplastic agents. In one preferred embodiment, the supplemental agent kills tumors cells by a mechanism other than apoptosis. For example, an antimetabolite, a purine or pyrimidine analogue, an alkylating agent, crosslinking agent (e.g., a platinum compound), and intercalating agent, and/or an antibiotic is administered in a combination therapy regimen. The supplemental drug is given before, after, or simultaneously with the methylol-containing agent. For example, the methylol transfer agent can be co-administered with a fluoro-pyrimidine, such as 5-fluoro-uracil (5-FU). Effective daily dosage amounts of a fluoro-pyrimidine may be in the range of about 0.1-1,000 mg per pharmaceutical dosage unit. Effective dosage amounts of 5-FU also may be in the range of about 100-5,000 mg/m$^2$ body surface area, preferably about 200-1,000 mg/m$^2$ body surface area, more preferably about 500-600 mg/m$^2$ body surface area. 5-FU typically is provided in 250 mg or 500 mg ampules for injection, or 250 mg capsules for oral administration.

In another embodiment, the apoptotic effect of methylol transfer agents can be enhanced by co-administration with a Fas-ligand. A Fas-ligand polypeptide is disclosed in U.S. Pat. No. 5,858,990. Therapeutically effective amounts of Fas-ligand generally will be within a range of about 0.01-1,000 mg/kg patient body weight, preferably about 0.1-200 mg 1 kg patient body weight, most preferable about 0.2-20 mg/kg patient body weight. The therapeutically effective amounts can be administered as dosages once per day, or multiple times per day such as two, three, four or more times per day.

In LN-18 cells taurultam (100 µg/ml) clearly enhanced apoptosis induced by 0.4 or 2.0 vol. % Fas-ligand. Example 1. This is the more striking as taurultam by itself did not impair the cell viability at this concentration. Thus, taurultam is able to enhance the effectiveness of the Fas-ligand induced apoptotic pathway. The same holds for taurolidine (100 µg/ml), although taurolidine alone did reduce cell viability at this concentration. Example 1. These results support the view that the apoptotic affect of taurultam and taurolidine is enhanced by Fas-ligand. When taurultam or taurolidine at a concentration of 100 µg/ml are combined with Fas-ligand, the total cell loss represents itself as the sum of that of Fas-ligand and of taurolidine or taurultam alone. Thus, the cytotoxicity of taurultam and taurolidine at this concentration appears to be additive to the Fas-mediated apoptosis. At lower concentrations, the apoptopic effect of taurolidine and taurultam are greatly enhanced, beyond an additive effect, by co-administration with the Fas-ligand.

The invention also includes treating a drug resistant tumor, e.g., a multiple drug resistant (MDR) tumor, in a mammal by administering to the mammal a methylol-containing compound. The tumor to be treated is a carcinoma or sarcoma. The drug resistant tumor is selected from the group consisting of a solid tumor, a non-solid tumor, and a lymphoma. For example, the drug resistant tumor is a breast cancer, ovarian cancer, colon cancer, prostate cancer, pancreatic cancer, CNS cancer, liver cancer, lung cancer, urinary bladder cancer, lymphoma, leukemia, or sarcoma.

According to another embodiment, a solution containing taurolidine and/or taurultam further contains taurin, in an amount within a range of about 1-20 g/l, preferably about 5 g/l.

A further embodiment provides methods for treating both primary liver tumors and metastases thereof, by direct administration of a solution containing a methylol transfer agent to the liver through a catheter installed in a hepatic vessel. By administering the methylol transfer agent in a solution that assists in maintaining liver function and non-ischemic conditions, therapy is directed to the affected organ, without unduly subjecting the organ to undue stress.

For treatment of primary liver tumors, the solution of methylol transfer agent may be administered through the hepatic artery, such that the therapeutic agent is carried into the organ for maximum effect. Alternatively, the solution can be supplied via the gastroduodenal artery, for delivery to the liver through the hepatic artery. The preferred solution for use in this embodiment is one that assists in maintaining liver function and minimizing stress to the organ associated with infusion of large volumes of methylol transfer agent solution. Solutions which may be used in the present invention are set forth in the Examples.

EXAMPLE 1

Isotonic Solution 2% Taurolidine

One suitable composition for intravenous drop infusion is shown below.
Isotonic sterile solution, 100 ml:
2.0 g Taurolidine
5.0 g PVP 16 PF UP aqua dest. ad solut. 100 ml. PH 7.2-7.3
Sterile-filtered and steam sterilization.

EXAMPLE 2

Isotonic Taurolin® Solution 2% Taurolidine with Taurin and electrolytes

Another suitable composition for intravenous drop infusion is shown below.
Isotonic sterile solution, 100 ml:
2.0 g Taurolidine
5.0 g PVP 17 PF UP
0.5 g Taurin
0.3 g Sodium chloride
Sterile-filtered and steam sterilization

EXAMPLE 3

Isotonic Taurolin® Ringer Solution 2% Taurolidine with Taurin and Electrolytes

Another suitable composition for intravenous drop infusion is shown below.
Isotonic sterile solution, 100 ml:
2.0 g Taurolidine
5.0 g PVP 17 PF UP
0.5 g Taurin
0.26 g Sodium chloride
0.0033 g Potassium chloride
0.004 g Calcium chloride 2H$_2$O
0.003 g Sodium hydrogen carbonate
Sterile-filtered and steam sterilization

EXAMPLE 4

Taurolin® Ringer-Lactate 2% Taurolidine with Taurin and Electrolytes

Another suitable composition for intravenous drop infusion is shown below.
Isotonic sterile solution, 100 ml:
2.0 g Taurolidine
5.0 g PVP 17 PF UP
0.5 g Taurin
0.20 g Sodium chloride
0.013 g Potassium chloride
0.009 g Calcium chloride 2H$_2$O
0.0033 g Sodium lactate 50% solution (Pharmacopeia Europea)
Sterile-filtered and steam sterilization

EXAMPLE 5

Taurultam Solution

One preferred solution comprises:
Lactobionic acid 35.830 g
Adenosine 1.340 g
Raffinose Pentahydrate 17.830 g
Hydroxyethyl starch (HES) PL 40/0.5 50.000 g
Glutathione 0.929 g
Allopurinol 0.136 g
Taurultam 10.000 g
Kcl 5.200 g
MgSO$_4$7H$_2$O 1.230 g
NaOH 25% GV to pH 7.8
NaOH pellets Merck 6482
Distalled water 900 ml The solution was sterilized from 16 minutes at 121° C. The pH after sterilization was 7.2, and pH of ready to use solution was 7.47.

EXAMPLE 6

Inducement of Apoptosis

Taurolidine and taurultam were tested for their ability to enhance apoptosis or induce cell death, alone and in combination with the Fas-ligand, in human malignant glioma cell lines. The two cell lines LN-18 and LN-229 represent validated model systems for apoptotic cell death with different sensitivities to Fas-ligand (Schlappbach and Fontana, 1997). These cell lines were therefore used to test the potential interaction of taurultam or taurolidine with the apoptotic pathway.

1) Reagents

Taurolidine (Batch Nr. 41692/7) and taurultam (Batch E/39024/4) were provided by Geistlich Pharma AG, Wolhusen, Switzerland. DME-Culture Medium and fetal bovine serum (FBS) were purchased from Gibco BRL, Basel, Switzerland. The cell proliferation assay WST-1 was purchased from Roche Diagnostics, Rotkreuz, Switzerland. Fas-ligand (supernatant from an overexpression system) and the human glioma cell lines LN-18 and LN-229 were kindly provided by Prof. A. Fontana, Institute of Clinical Immunology, University Hospital, Zurich, Switzerland 2) Cell Lines The cell lines LN-18 and LN-229 were cultured at 37° C. and 5% $CO_2$ in DMEM containing 5% FBS and 2 mM glutamin (10 cm plates NUNCLON 15035). In the experiments in which Fas-ligand was tested by itself, about $1 \times 10^4$ cells were plated per well in 96-well plates (NUNCLON 167008) resulting in a confluency of about 60% on the following day (17 h incubation). In all other experiments about $1.5 \times 10^4$ cells were plated which resulted in a confluency of about 90% on the following day (17 h incubation). Fas-ligand was added as supernatant indicated as % volume (vol %) of total culture volume.

3) Cell Viability Test

LN-18 and LN-229 cells were incubated in 50 μl medium in the absence or presence of either Fas-ligand, taurultam, taurolidine or respective combinations thereof. After a 17 h incubation the cell viability was determined by adding 50 μl medium containing a double concentrated WST-1 reagent. The coloration resulting from the activity of the mitochondrial succinate reductase, was measured in an ELISA reader at 450 nm using a reference wavelength of 690 nm.

The human malignant glioma cell lines LN-18 and LN-229 were used to test the ability of taurolidine and taurultam to affect cell viability and/or to enhance Fas-ligand induced apoptosis. The two human malignant glioma cell lines, LN-18 and LN-229 had previously been reported to display different sensitivity to the apoptotic effect of Fas-ligand (Schlappbach and Fontana, 1997).

1) Sensitivity of LN-18 and LN-229 to Fas-ligand

In a first set of experiments it was investigated whether the different sensitivity of LN-18 and LN-229 to Fas-ligand was reproduced under our experimental conditions. The two cell lines were incubated over night (17 h) in 96 well plates containing $1 \times 10^4$ cells per well with increasing concentrations of Fas-ligand (3.1, 6.25, 12.5, 25.0 and 50 vol. %). In the absence of Fas-ligand the cells reached about 60% confluency after overnight incubation. In the presence of Fas-ligand LN-18 was extremely sensitive, displaying more than 90% loss of cell viability in the presence of only 6.25 vol. % Fas-ligand. Even at 3.1%, an approximately 85% reduction in cell viability was observed. In contrast, the viability of LN-229 cells was not greatly affected by 6.25 vol. % Fas-ligand (approximately 10% reduction) and was reduced only at higher concentrations with a maximum of 40% cell loss in the presence of the highest concentration of Fas-ligand tested (50 vol. %).

2) Influence of Taurultam on Fas-ligand Induced Apoptosis in LN-18-Cells

LN-18 cells were incubated for 17 h with increasing concentrations of taurultam (5, 20, 100 μg/ml) in the absence and presence of two concentrations of Fas-ligand (0.4 vol. % and 2.0 vol. %). Taurultam by itself even at the highest concentration tested (100 μg/ml) did not affect the cell viability (an approximately 5% reduction was observed at 5 and 20 μg/ml, and viability actually appeared to increase at 100 μg/ml). In the presence of 0.4 vol. % Fas-ligand alone cell viability was reduced by only about 10%, an effect which remained unchanged in the presence of 5 or 20 μg/ml taurultam. However cell viability was strongly decreased when 0.4 vol. % Fas-ligand was coincubated with of 100 μg/ml taurultam. When the Fas-ligand was added at a higher concentration (2.0 vol. %) apoptosis was induced in 60% of the cells by Fas-ligand alone. This effect was also increased by taurultam at 100 μg/ml but not at 5 or 20 μg/ml. Thus, taurultam is able to enhance the apoptotic effect of Fas-ligand in LN-18 cells at a concentration (100 μg/ml) which by itself did not affect cell viability.

3) Influence of Taurolidine on Fas-ligand Induced Apoptosis in LN-18 Cells

LN-18 cells were incubated for 17 h with either 0.4 or 2.0 vol. % Fas-ligand in the absence and presence of increasing concentrations of taurolidine (5, 20, 100 μg/ml). Taurolidine by itself did not appreciably affect cell viability yielding a reduction by only 10% at the highest concentration tested (100 μg/ml). In the presence of Fas-ligand alone (0.4% or 2.0%) the cell viability was affected in the same way as described above. The cell viability was further reduced by taurolidine but only at the highest concentration tested (100 μg/ml). Thus, taurolidine was able to enhance the effect of Fas-ligand on LN-18 cells at a concentration (100 μg/ml) which did not appreciably affect cell viability per se.

4) Influence of Taurultam on Fas-ligand Induced Apoptosis in LN-229 Cells

The incubation of LN-229 cells for 17 h with taurultam alone had no effect at and 20 μg/ml but reduced cell viability by 35% at 100 μg/ml. When the LN-229 cells were incubated with Fas-ligand alone (10% or 50%) the cell viability was reduced by only about 20% in the presence of a high concentration of Fas-ligand (50 vol. %). When taurultam was added at concentrations which were inactive per se (5 and 20 μg/ml) no change in the effectiveness of the Fas-ligand (10 or 50 vol. %) was observed. It was only at the highest concentration of taurultam (100 μg/ml) that Fas-ligand induced cell loss was further enhanced. Thus, the results with LN-229 demonstrate the ability of taurultam to enhance the destruction of cells in the presence of Fas-ligand.

5) Influence of Taurolidine on Fas-ligand Induced Apoptosis in LN-229 Cells

The exposure of LN-229 cells to taurolidine alone for 17 h caused a strong loss of cell viability by about 70% at the highest concentration tested (100 μg/ml). Thus, LN-229 cells were more sensitive to taurolidine than LN-18 cells. When co-incubated with Fas-ligand (10 vol. %) cell destruction was enhanced by taurolidine at 100 μg/ml. At 50 vol. % Fas-ligand the effect was more pronounced and apparent even for taurolidine 20 μg/ml.

EXAMPLE 7

Use and Application of Taurolidine and/or Taurultam for the Treatment and/or Prophylaxis of Tumors of the Central Nervous System 1. Tumor Cells Used for the Experiments
For experiments, C6 glial tumor cells, HT22 neuronal tumor cells, U373 human glioma/glioblastoma tumor cells and cells derived from patients with glioblastoma were used.

2. Preparation of Patient-derived Tumor Cells
Tumor cells derived from patients with glioblastoma were obtained intraoperatively. Tumor tissue was stored in RPMI 1640 medium without FCS. Tissue was then sub cultured in 15 ml Falcon flasks; adding 0.025% trypsin with PBS, followed by incubation at 37° C. After this, RPMI 1640 with FCS was added and centrifugation performed. The next step was incubation with DNAse, resuspension and dissociation, followed by washing step in medium to remove DNAse. Cells were then cultured in Falcon flasks.

3. Method of Anti-neoplastic Action of Taurolidine and/or Metabolites
Ultrastructurally, shrinkage of cytoplasm, condensation and marginalization of chromatin could be observed. These changes were already apparent at 30 minutes of incubation with 0.1 µg/ml taurin and increased strikingly over time and with concentration of taurolidine. Mitochondria were not affected ultrastructurally. Flow cytometry showed an initial increase in the G0/G1 peak and S-phase starting at 30 minutes. These initial changes were followed by a decrease in forward light and side scatter. In addition, concentration-dependent fragmentation of DNA started at 60 minutes. Following 24 hours, fragmentation of the DNA was nearly complete. At concentrations of 2.0 µg/ml taurolidine and more, the changes in cell size was only marginal.

The described results in combination with the results of special dying methods (Leucostat preparation) suggests an apoptotic mechanism of tumor cell death. Normal brain cells were not affected by incubation with taurolidine or taurultam in concentrations of up to 4 µg/ml for up to 5 days.

EXAMPLE 8

Two-cycle Dosing Schedule for Treating Patients with Cancer Using Intervenous Taurolidine 2%

Four bottles (250 ml each) of 2% taurolidine solution are administered intravenously to patients with cancer, at a rate of 40 drops per minute, one bottle every six hours. The dosing cycle consists of an administration phase of daily infusions for one week, followed by a non-administration phase of two weeks, then followed by another administration phase of four bottles per day as previously indicated. Efficacy of taurolidine 2% solution administered intravenously has been found to be particularly good with 25-28 bottles of 250 ml taurolidine 2% solution being instilled per cycle.

EXAMPLE 9

Four-cycle Dosing Schedule for Treating Patients with Malignant Gliomas Using Intravenous Taurolidine 2%

The treatment comprises a minimum of 4 cycles. Each cycle is 7 days long, and is comprised as follows:
1. First Cycle
  a. Intravenous infusion of 250 ml taurolidine 2% and 250 ml full electrolyte solution via the central vein catheter with an infusion time of 60 minutes.
  b. If this therapy causes an elevated liver count, it is necessary to increase the infusion time to 90 or 120 minutes.
  c. 60-minute break
  d. Repeat the therapies under a or b and c for a total of 6 times per day.
  e. At an infusion time of 60 minutes the duration of the daily infusion program per 250 ml of taurolidine is 11 hours, at 90 minutes of infusion time 14 hours, and at 120 minutes of infusion time 17 hours. No drug is administered for the remainder of the time.
  f. rest phase
2. Subsequent Cycles
  a. Intravenous infusion of 250 ml taurolidine 2% and 250 ml full electrolyte solution via the central vein catheter with an infusion time of 60 minutes.
  b. If this therapy causes an elevated liver count, it is necessary to increase the infusion time to 90 or 120 minutes.
  c. 60 minute break
  d. Repeat the therapies under a or b and c for a total of 4 times per day.
  e. At an infusion time of 60 minutes the duration of the daily infusion program per 250 ml of taurolidine is 7 hours, at 90 minutes of infusion time 9 hours, and at 120 minutes of infusion time 11 hours. No drug is administered for the remainder of the time.

EXAMPLE 10

Therapy of Glioblastoma with Taurolidine (Single Case Observation)

The following is a case involving treatment of a single individual with a single treatment cycle.

Patient: "F.D.," male, 59 years
Diagnosis: large (8×8×8 cm) malignant glioma bifrontal with affection of the corpus callosum ("butterfly glioma").
Procedure prior to treatment with taurolidine: Patient was referred to Neurosurgical departments in Heidelberg and Wurzburg, operation was refused, radiation and chemotherapy were refused by the patient.
Prior treatment: oral corticosteroids.
Planned Treatment: Taurolidine intravenously
Chief complaints on admission: Diffuse headache, urinary incontinence, blurred vision, motor aphasia, gait disturbance, impaired memory.
Neurological examination on admission: Awake-somnolent, alert, impaired vision, nearly complete motor aphasia, apraxia, gait disturbance, urinary incontinence, severe mnesic and concentration deficits
Karnofsky index on admission: 20-30
MRI at Day 1 of treatment (pre treatment): Bifrontal space occupying lesion (ca. 8×8×8 cm) with irregular shape and ring like contrast enhancement and destructive affection of the corpus callosum. The marked space occupying effect leads to disappearance of nearly all reserve spaces.
Treatment
Day 1: Informed consent; Blood samples; MRI.
Day 2: Insertion of a central venous line; Chest X-ray.
Days 3-8: Intravenous administration of 4×250 ml of 2% taurolidine/day within 2 hours, followed by an interval of 4 hours; Blood samples twice daily; Substitution of electrolytes.
Day 9: Intravenous administration of 1×250 ml of 2% Taurolidine within 2 hours; Discharge.
Treatment Summary:
In total, 25×250 ml of 2% taurolidine (125 g taurolidine) were administered without side effects. Electrolytes and fluid were substituted according to the results of the blood samples.

Chief complaints on discharge: Headache improved, no urinary incontinence, vision improved, gait disturbance improved, motor aphasia slightly improved, impaired memory.

Neurological examination on discharge: Awake, alert, vision improved, motor aphasia slightly improved, gait disturbance improved, apraxia slightly improved, no urinary incontinence, severe mnesic and concentration deficits Karnofsky index on discharge: 40-50

In view of the dramatic improvement observed in the patient's condition after a single treatment cycle, it is expected that an infusion regime of at least two cycles will provide the desired therapeutic effect.

EXAMPLE 11

Treatment of Severe Glioblastoma Multiforme Grade IV

Prior to treatment the patient exhibited severe glioblastoma multiforme grade IV, left temporal lobe affected. The tumor was prominent in computer tomography pictures of the patient's cranium, prior to treatment. The patient's cranium was imaged in a T2-weighted picture sequence in axial, sagittal and coronary layer orientation as well as T1-weighted picture sequence in axial layer orientation natively and in axial, coronary and sagittal layer orientation after contrast medium application as well as MR spectroscopy.

The patient was treated with four treatment cycles each consisting of a seven-day infusion phase of a daily dose of 20 g taurolidine (4×250 ml 2% taurolidine solution) and a two-day rest phase. After the four cycles, the patient underwent an additional two-day infusion phase. Regular computer tomography images of the patient's cranium were taken during treatment.

By the end of the second treatment cycle (200 g taurolidine administered), brain edema was noticeably reduced. By the end of third treatment cycle (300 g taurolidine administered), tumor growth had stopped. After the completion of the entire course of treatment (600 g taurolidine administered), the tumor was shown by computer tomography to be almost completely disintegrated. Little or no necrosis was observed during the course of treatment, indicating that the tumor reduction was the result of apoptosis.

EXAMPLE 12

Treatment of Brain Tumors with Direct Application of Taurolidine/Taurultam

The methylol transfer agent is applied directly to the tumor cavity using taurolidine/taurultam containing tubes consisting of several segments with semipermeable membrane.

Following total or partial tumor removal, a special tube is implanted in the tumor cavity, so that the end of this tube lies subgaleal. The tube includes various segments of semipermeable material, which contains taurolidine/taurultam and can be refilled via a subgaleal port.

EXAMPLE 13

Treatment of Inoperable Glioblastoma Infiltration of Basal Ganglia

A forty year old male patient with inoperable glioblastoma infiltration in the basal ganglia was treated with a regimen of 6 dosing cycles, each with administration phases of 5 days, with each administration phase separated by a non-administration phase of 2 days. During each day of administration, 250 ml of taurolidine 2% solution was intravenously administered to the patient 4 times daily. This regimen surprisingly and unexpectedly resulted in a marked size-reduction of the tumor, and disappearance of perifocal edema.

I claim:

1. A method of inhibiting growth of a central nervous system (CNS) tumor cell in a mammal comprising administering to said mammal a solution comprising 0.5% or 1% taurolidine, taurultam, or a mixture thereof, said solution further comprising a plurality of electrolytes, so as to inhibit growth of the CNS tumor cell in said mammal.

2. The method of claim 1 wherein said electrolytes provide ions comprising sodium, potassium, $Mg^{++}$, $Cl^-$ or $Acetate^-$.

3. The method of claim 1 wherein said electrolytes comprise NaCl, KCl, $CaCl_2$ and $NaHCO_3$.

4. The method of claim 1 wherein said solution is isotonic.

5. The method of claim 1 wherein said solution contains about 0.5% by weight taurultam.

6. The method of claim 1 wherein said solution contains about 1% by weight taurultam.

7. A method of inhibiting growth of a malignant tumor cell in a mammal comprising administering to said mammal a solution comprising taurolidine, taurultam, or a mixture thereof, said solution further comprising the electrolytes NaCl, KCl, $CaCl_2$ and $NHCO_3$, so as to inhibit growth of the tumor cell in said mammal.

8. The method of claim 7 wherein said solution further comprises the electrolytes $Mg^{++}$, or $Acetate^-$.

9. The method of claim 7 wherein said solution is isotonic.

10. The method of claim 7 wherein said solution contains about 2% by weight taurolidine.

11. The method of claim 7 wherein said solution contains about 0.5% by weight taurultam.

12. The method of claim 7 wherein said solution contains about 1% by weight taurultam.

13. A method of inhibiting growth of a cancer cell in a mammal comprising:
   A) administering to said mammal a first solution comprising 0.5% to 2% of a cancer-inhibiting methylol-containing compound comprising taurolidine, taurultam or a mixture thereof, said first solution further comprising a first combination comprising at least one amino acid in combination with at least one physiologically acceptable electrolyte, so as to inhibit growth of the cancer cell in said mammal; or
   B) administering to said mammal another solution containing 0.5% to 2% of said cancer-inhibiting methylol-containing compound comprising taurolidine, taurultam or a mixture thereof, and concurrently administering to said mammal a further solution comprising a second combination comprising a plurality of physiologically acceptable electrolytes or said first combination comprising at least one said amino acid in combination with at least one said physiologically acceptable electrolyte, so as to inhibit growth of the cancer cell in said mammal.

14. The method of claim 13 wherein, when said first solution is administered, said first solution contains said first combination at a concentration sufficient to render said first solution substantially isotonic, and when said another solution is administered, prior to administration to said mammal, said another solution is blended with said further solution so as to form a mixed solution which is substantially isotonic.

15. The method of claim 14 wherein said electrolyte or electrolytes provide ions selected from the group consisting of $Na^+$, $K^+$, $Mg^{++}$, $Cl^-$, $H_2PO_4^-$, $Acetate^-$, $HCO_3^-$, and mixtures thereof.

16. The method of claim 14 wherein said electrolyte or electrolytes are selected from the group consisting of NaCl, KCl, $CaCl_2$, $NaHCO_3$, and mixtures thereof.

17. The method of claim 14 wherein said first solution or said another solution contains about 1.7-2.3% by weight taurolidine.

18. The method of claim 14 wherein said first solution or said another solution contains about 1.8-2.2% by weight taurolidine.

19. The method of claim 14 wherein said first solution or said another solution contains about 1.9-2.1% by weight taurolidine.

20. The method of claim 14 wherein said first solution or said another solution contains about 2% by weight taurolidine.

21. The method composition of claim 14 wherein said first solution or said further solution further contains an amount of a colloid effective to render said first solution or said mixed solution substantially iso-oncotic.

22. The method of claim 21 wherein said colloid is present in said first solution or said mixed solution in an amount of about 1-10% by weight.

23. The method of claim 22 wherein said colloid is PVP having an average molecular weight of about 1,000-15,000.

24. The method of claim 23 wherein said average molecular weight is about 9,000.

25. The method of claim 14 wherein said first solution or said mixed solution further includes about 0.1-3% by weight of at least one amino acid.

26. The method of claim 25 wherein said at least one amino acid is taurine.

27. The method of claim 26 wherein said first solution or said mixed solution contains about 0.3-1% by weight taurine.

28. The method of claim 27 wherein said first solution or said mixed solution contains about 0.4-0.6% by weight taurine.

29. The method of claim 28 wherein said first solution or said mixed solution contains about 0.5% by weight taurine.

30. The method of claim 14 wherein said first solution or said mixed solution includes about 0.1-1% by weight taurultam.

31. The composition of claim 30, wherein said first solution or said mixed solution includes about 0.2-0.5% by weight taurultam.

* * * * *